United States Patent [19]
Kodama

[11] Patent Number: 5,731,593
[45] Date of Patent: Mar. 24, 1998

[54] ION IMPLANTATION METHOD AND ION IMPLANTATION SYSTEM USED THEREFOR

[75] Inventor: Shuichi Kodama, Tokyo, Japan

[73] Assignee: NEC Corporation, Tokyo, Japan

[21] Appl. No.: 808,438

[22] Filed: Feb. 28, 1997

[51] Int. Cl.[6] ................................................ G01N 23/225
[52] U.S. Cl. ................................. 250/492.21; 250/251
[58] Field of Search ........................... 250/492.21, 492.2, 250/398, 251

[56] References Cited

U.S. PATENT DOCUMENTS 5,241,186  8/1993  Yunogami et al. ............... 250/492.2

*Primary Examiner*—Kiet T. Nguyen
*Attorney, Agent, or Firm*—Sughrue, Mion, Zinn, Macpeak & Seas, PLLC

[57] ABSTRACT

An ion implantation method is provided, which is able to suppress unwanted positive charges built-up on the surface of an ion-implanted semiconductor wafer. First, a wafer holder kept at a first electric potential and an electrode kept at a second electric potential higher than the first electric potential are prepared. A semiconductor wafer is then placed on the holder to be kept at the first electric potential. The holder is moved so that the wafer held on the holder is located at a first position. A beam of dopant ions is irradiated to the wafer at the first position to thereby implant the dopant ions into the wafer. The holder is then moved so that the wafer thus ion-implanted is located at a second position where the wafer is in the vicinity of the electrode. An electric field is generated between the wafer and the electrode due to the difference between the first and second electric potentials. Positive charges that have been built up on a surface of the ion-implanted wafer are expelled therefrom due to the electric field.

8 Claims, 4 Drawing Sheets

ION IMPLANTATION METHOD AND ION IMPLANTATION SYSTEM USED THEREFOR

BACKGROUND OF THE INVENTION

1. Field of the Invention

The present invention relates to ion implantation in semiconductor device fabrication and more particularly, to an ion implantation method that is able to suppress unwanted positive charges built-up on the surface of an ion-implanted semiconductor wafer, and an ion implantation system used for the method.

2. Description of the Prior Art

Ion implantation is a process of implanting n-or p-type dopant ions into a semiconductor wafer by irradiating a beam of the dopant ions to the wafer in semiconductor device fabrication. The implanted dopant ions form a dopant layer in the wafer.

With the ion implantation process, it has been known that unwanted positive charges tend to build up on the surface of the ion-implanted wafer due to the irradiated dopant ions having positive charges. The built-up positive charges will cause some disadvantages that an insulator layer formed on the surface of the wafer is damaged or broken and that the path of the subsequent beam of the dopant ions is deflected.

To remove these disadvantages, conventionally, the so-called "electron shower" technique has been developed and employed. The "electron shower" technique is a technique that electrons, which are emitted from a filament, are incorporated with a beam of dopant ions and the incorporated electrons are irradiated to the wafer together with the dopant ions, thereby neutralizing the built-up positive charges on the wafer.

FIG. 1 schematically shows a conventional ion implantation method that uses the "electron shower" technique. In FIG. 1, there are a wafer disk 111 for holding semiconductor wafers 110, an electron-beam irradiation subsystem (not shown), and an electron shower subsystem 120 in a vacuum chamber 130.

The wafer disk 111, which is made of an electrically conductive material, has a horizontally extending shaft 111a and a surface 111b located in a vertical plane. The disk 111 is supported by the shaft 111a and is rotated around the shaft 111a at a fixed speed, as shown by an arrow 118. Further, the disk 111 is moved upward and downward, as shown by an arrow 119. The distance of the vertical movement is designed to be approximately equal to the diameter of the wafers 110.

A plurality of semiconductor wafers 110 to be ion-implanted are held on the surface 111b. These wafers 110 are arranged along a circle concentric with the shaft 111a at regular intervals.

The disk 111 is electrically connected to the ground potential. The wafers 110 held on the disk 111 are contacted with the surface 111b of the disk 111 and therefore, the wafers 110 also are kept at the ground potential.

The electron-beam irradiation subsystem generates a beam 125 of n- or p-type dopant ions 102 having positive charges from an ion source (not shown), and then irradiates the beam 125 thus generated to the wafers 110 held on the wafer disk 111. The beam 125 horizontally travels toward the disk 111. The beam 125 is designed to irradiate one of the wafers 110 located at the top position of the rotating disk 111. The beam 125 itself does not scan the wafers 110.

The rotation along the arrow 118 and the vertical movement along the arrow 119 of the wafer disk 111 enable the scanning of the beam 125 over the whole surface of each of the wafers 110. Specifically, the rotation of the disk 111 realizes the horizontal scanning of each of the wafers 110, and the vertical movement of the disk 111 realizes the vertical scanning thereof. Thus, the beam 125 is able to scan the whole surface of each of the wafers 110.

Further, the rotation of the disk 111 makes it possible that all of the wafers 110 held on the disk 111 are successively subjected to the same scanning of the beam 125.

The electron shower subsystem 120 has a filament 121 made of tungsten (W) or the like, and a target 123 for generating an electron shower. The filament 121 and the target 123 are fixed in the camber 130 to be opposite to each other, and they are arranged at each side of the ion beam 125.

An electric current 122 flows through the filament 121 due to a voltage applied thereto, thereby emitting primary electrons (i.e., thermoelectrons) 103a from the filament 121. The primary electrons 103a thus emitted travel vertically toward the target 123 across the path of the ion beam 125 and then, they are collide with the target 123. Due to the collision of the primary electrons 103a with the target 123, secondary electrons 103b are generated and emitted from the target 123 toward the beam 125.

The secondary electrons 103b thus emitted are then incorporated into the ion beam 125 due to the electric pulling force and then, they are irradiated to the wafers 110 as the "electron shower" together with the dopant ions 102. The irradiated positive ions 102 are implanted into the wafers 110. At the same time, the irradiated secondary electrons 103b neutralize the positive charges 102a that have been built up on the surfaces of the wafers 110, thereby eliminating or suppressing the buildup of the positive charges 102a.

For example, when the ion type is boron ($^{11}B^+$), the acceleration energy of the dopant ions 102 is 40 keV, the dose of the implanted ions 102 is $1\times10^{16}$ cm$^{-2}$, and the beam current of the ions 102 is 7 mA, the filament current 122 is set as 10 mA.

The above conventional ion implantation method has the following problem:

Specifically, as the operating period of the filament 121 becomes long, the filament 121 increasingly tends to be cut due to the expiration of its lifetime. Therefore, when the filament 121 has been cut, or when a specific operating time has been passed even if no cut of the filament 121 occurs, the operating filament 121 needs to be replaced with a new one.

This means that the maintenance of the ion-implantation system is complicated and troublesome, and that an inactive time of the ion implantation system occurs, thereby decreasing the throughput or productivity of the ion implantation process.

SUMMARY OF THE INVENTION

Accordingly, an object of the present invention is to provide an ion implantation method and an ion plantation system that are able to suppress unwanted positive charges built-up on the surface of an ion-implanted semiconductor wafer.

Another object of the present invention is to provide an ion implantation method and an ion implantation system that are able to dispense with the conventional electron shower technique.

According to a first aspect of the present invention, an ion implantation method is provided, which includes the following steps:

A wafer holder kept at a first electric potential and an electrode kept at a second electric potential higher than the first electric potential are prepared. A semiconductor wafer is placed on the holder to be kept at the first electric potential.

The holder is moved so that the wafer held on the holder is located at a first position. A beam of dopant ions is irradiated to the wafer at the first position to thereby implant the dopant ions into the wafer.

The holder is then moved so that the wafer thus ion-implanted is located at a second position where the wafer is in the vicinity of the electrode. An electric field is generated between the wafer and the electrode due to the difference between the first and second electric potentials.

Positive charges that have been built up on a surface of the ion-implanted wafer are expelled therefrom due to the electric field.

With the ion implantation method according to the first aspect of the present invention, the wafer is held on the holder to be kept at the first electric potential and then, it is irradiated by the beam of the dopant ions at the first position. Subsequently, the holder with the ion-implanted wafer is moved to the second position where the wafer is in the vicinity of the electrode.

Since the electrode is kept at the second electric potential higher than the first potential of the wafer, an electric field directing from the electrode toward the wafer is generated between the wafer and the electrode. This electric field has a function expelling the positive charges that have been built up on a surface of the ion-implanted wafer.

Consequently, the number of the built-up positive ions on the ion-implanted wafer decreases, thereby suppressing the built-up positive charges from the wafer.

Further, since the electric field generated between the electrode and the wafer suppresses the built-up positive charges on the wafer, the ion implantation process is able to performed without the use of the conventional electron shower technique.

In a preferred embodiment of the method according to the first aspect, the wafer holder is formed by a rotatable and movable disk having a shaft and a surface. The disk is rotated around the shaft of the disk and moved along the surface of the disk during an ion-implantation process, so that the beam of the dopant ions scan the whole surface of the wafer.

In another preferred embodiment of the method according to the first aspect, the disk is capable of holding another wafer on the surface of the disk so that the two wafers are arranged along a circle concentric with the shaft of the disk at regular intervals.

In still another preferred embodiment of the method according to the first aspect, the electrode has a shape like a flat plate whose width is approximately equal to the diameter of the wafer or greater and whose length is approximately equal to the sum of the diameter of the wafer and a stroke length of the movement of the wafer holder.

According to a second aspect of the present invention, an ion implantation system is provided, which includes a vacuum chamber, a wafer holder provided in the chamber, an ion-beam irradiation subsystem mounted in the chamber, and an electrode fixed in the chamber.

The holder is kept at a first electric potential. A semiconductor wafer to be ion-implanted is held on the holder to be kept at the first potential. The holder is movable so that the wafer held on the holder is located at a first position and a second position.

The ion-beam irradiation subsystem generates a beam of dopant ions and irradiates the beam thus generated to the wafer held on the holder at the first position.

The electrode is kept at a second electric potential higher than the first electric potential.

The wafer held on the holder is in the vicinity of the electrode at the second position. An electric field is generated between the wafer and the electrode due to the difference between the first and second electric potentials.

Positive charges that have been built up on a surface of the ion-implanted wafer are expelled therefrom due to the electric field.

With the ion implantation system according to the second aspect of the present invention, first, the wafer is held on the holder to be kept at the first electric potential and then, it is irradiated by the beam of the dopant ions at the first position. Subsequently, the holder with the ion-implanted wafer is moved to the second position where the wafer is in the vicinity of the electrode.

Since the electrode is kept at the second electric potential higher than the first potential of the wafer, the electric field directing from the electrode toward the wafer is generated between the wafer and the electrode. This electric field has a function expelling the positive charges that have been built up on a surface of the ion-implanted wafer.

Consequently, the number of the built-up positive ions on the ion-implanted wafer decreases, thereby suppressing the built-up positive charges from the wafer.

Further, since the electric field generated between the electrode and the wafer suppresses the built-up positive charges on the wafer, the ion implantation process is able to be performed without the use of the conventional electron shower technique.

In a preferred embodiment of the system according to the second aspect, the wafer holder is formed by a rotatable and movable disk having a shaft and a surface. The disk is rotated around the shaft of the disk and moved along the surface of the disk during an ion-implantation process so that the beam of the dopant ions scan the whole surface of the wafer.

In another preferred embodiment of the system according to the second aspect, the disk is capable of holding another wafer on the surface of the disk so that the two wafers are arranged along a circle concentric with the shaft of the disk at regular intervals.

In still another preferred embodiment of the system according to the second aspect, the electrode has a shape like a flat plate whose width is approximately equal to the diameter of the wafer or greater and whose length is approximately equal to the sum of the diameter of the wafer and a stroke length of the movement of the holder.

BRIEF DESCRIPTION OF THE DRAWINGS

In order that the present invention may be readily carried into effect, it will now be described with reference to the accompanying drawings.

DETAILED DESCRIPTION OF THE PREFERRED EMBODIMENTS

Figure 1:
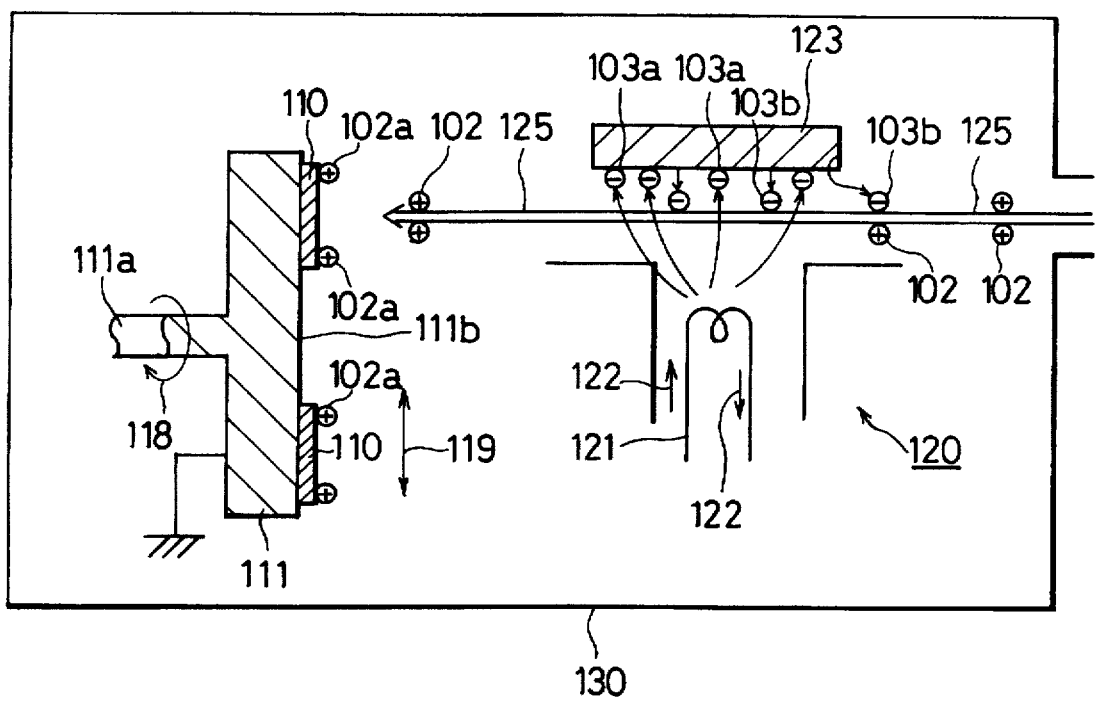
FIG. 1 is a schematic view showing an elevation of a conventional ion-implantation method.

A preferred embodiment of the present invention will be described below referring to the drawings attached.

An ion implantation system according to an embodiment of the present invention is shown in FIGS. 2, 3, 4A, and 4B. This system includes a vacuum chamber 30, a wafer disk 11 provided in the chamber 30, an ion-beam irradiation subsystem 9 mounted in the chamber 30, and an electrode 12 fixed in the chamber 30.

Here, the wafer disk 11 is made of an electrically conductive material. The disk 11 is electrically connected to the ground, in other words, it is kept at the ground potential.

The disk 11 has a horizontally extending shaft 11a and a surface 11b located in a vertical plane. The disk 11 is supported by the shaft 11a and is rotated around the shaft 11a at a fixed speed, as shown by an arrow 18. Further, the disk 11 is moved upward and downward, as shown by an arrow 19.

A plurality of semiconductor wafers 10 to be ion-implanted are held on the surface 11b. These wafers 10 are arranged along a circle concentric with the shaft 11a at regular intervals, as clearly shown in FIG. 2.

The wafers 10 held on the disk 11 are directly contacted with the surface 11b of the disk 11 and therefore, the wafers 10 also are kept at the ground potential.

The rotation along the arrow 18 and the vertical movement along the arrow 19 of the wafer disk 11 enable the scanning of the beam 15 over the whole surface of each of the wafers 10. Specifically, the rotation of the disk 11 realizes the horizontal scanning of each of the wafers 10, and the vertical movement of the disk 11 realizes the vertical scanning thereof. Thus, the beam 15 is able to scan the whole surface of each of the wafers 10.

Further, the rotation of the disk 11 makes it possible that all of the wafers 10 held on the disk 11 are successively subjected to the same scanning of the beam 15.

The distance of the vertical movement of the disk 11 is designed to be approximately equal to the diameter D of the wafers 10 for the purpose of the scanning.

The ion-beam irradiation subsystem 9 generates a beam 15 of n- or p-type dopant ions 2 having positive charges from an ion source (not shown), and then irradiates the beam 15 thus generated to the wafers 10 held on the wafer disk 11. The beam 15 horizontally travels toward the disk 11. This subsystem 9 may have a configuration.

Here, the beam 15 is designed to irradiate one of the wafers 10 located at the top position of the rotating disk 11. The beam 15 itself does not scan the wafers 10.

The electrode 12 is used for suppressing or removing the unwanted positive charges 2a built-up on the respective surfaces of the wafers 10. The electrode 12 is fixed by a supporting member 12a in the chamber 30. The electrode 12 is electrically connected to a dc power supply 13 (supply voltage: +V volt) provided outside the vacuum chamber 30 with wiring lines 20. Therefore, the electrode 12 is kept at a positive electric potential +V (volt), which is higher than the ground potential. The wiring lines 20 penetrate a hole 14 of the chamber 30. The hole 14 is hermetically sealed.

The electrode 12 is made of a flat metal plate whose width W is approximately equal to the diameter D of the wafers 10 and whose length L is approximately equal to the sum of the diameter D of the wafers 10 and a stroke length S of the vertical movement of the wafer disk 11. In other words, $W \approx D$ and $L \approx (D+S)$.

The flat-plate electrode 12 is positioned to be apart from and opposite to the wafers 10 held on the disk 11. The gap between the electrode 12 and the wafers 10 is G. The gap G is maintained over the full stroke of the vertical movement of the disk 11.

Figure 2:
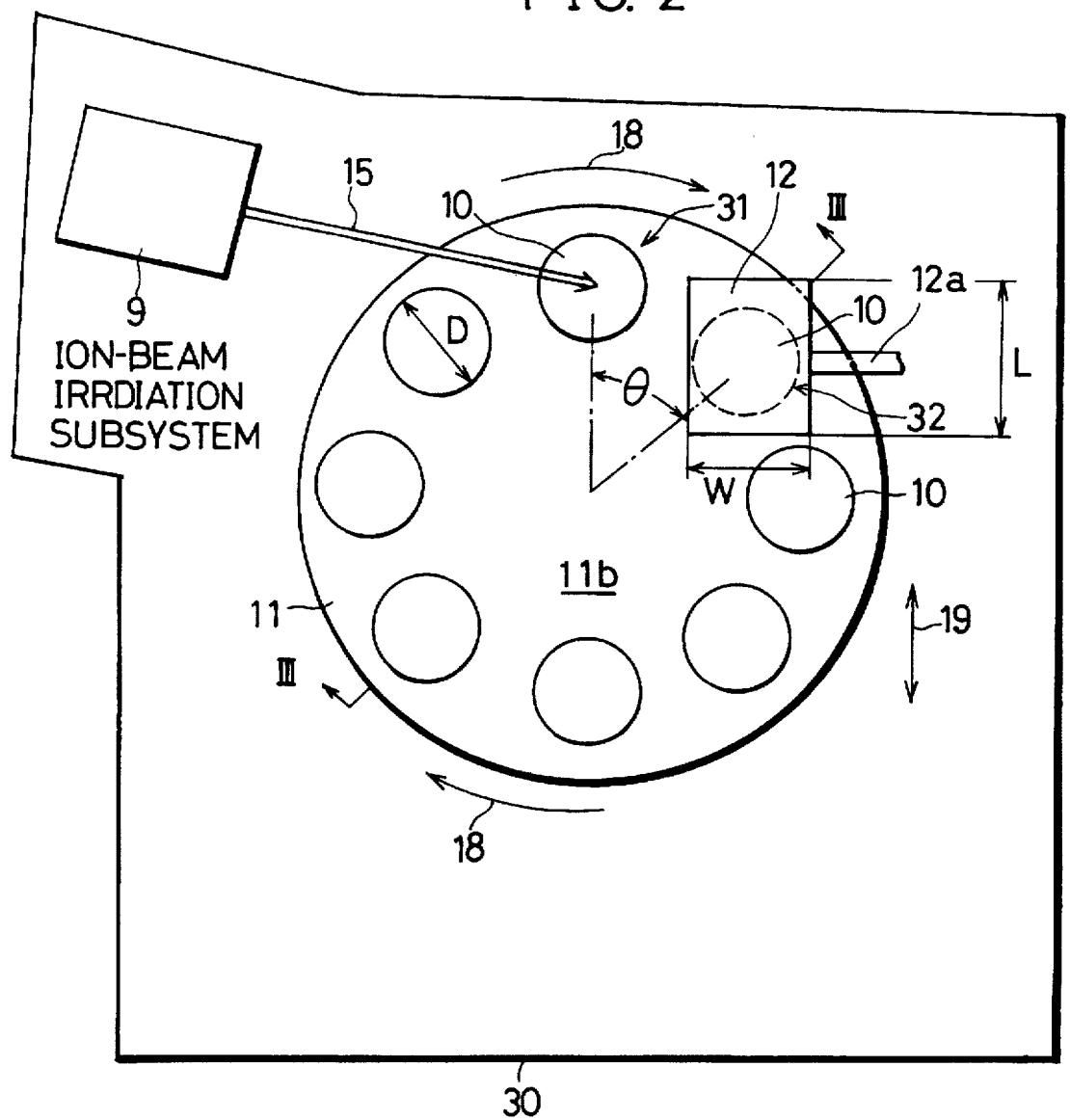
FIG. 2 is a schematic view of a wafer holder of an ion-implantation system according to an embodiment of the present invention.
Figure 3:
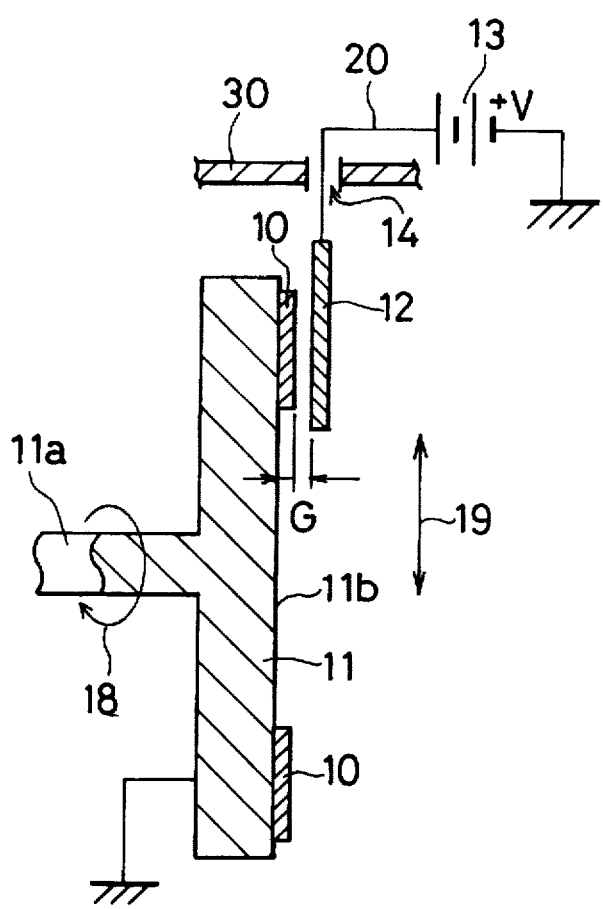
FIG. 3 is a schematic, cross-sectional view along the line III—III in FIG. 2.
Figure 4A:
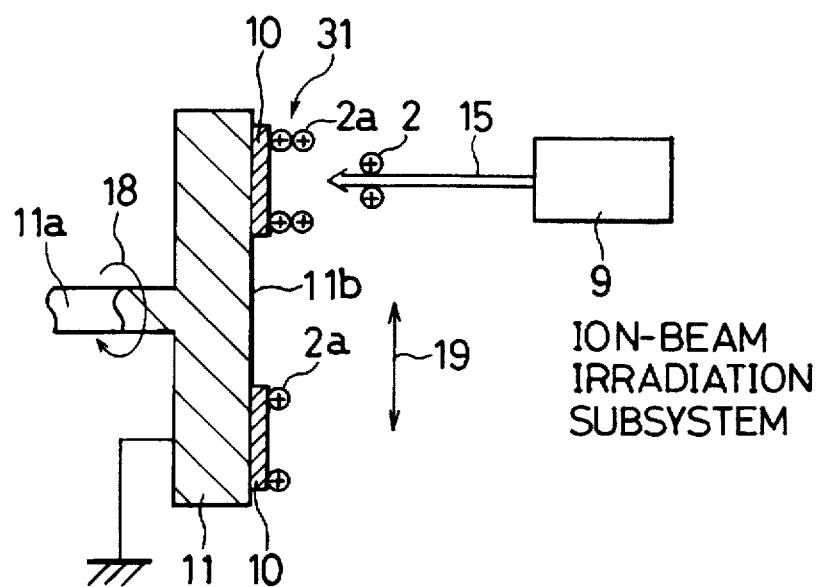
FIG. 4A is a schematic, cross-sectional view of the wafer holder of the ion-implantation system according to the embodiment of FIG. 2, in which the ion beam is irradiated to the wafer.
Figure 4B:
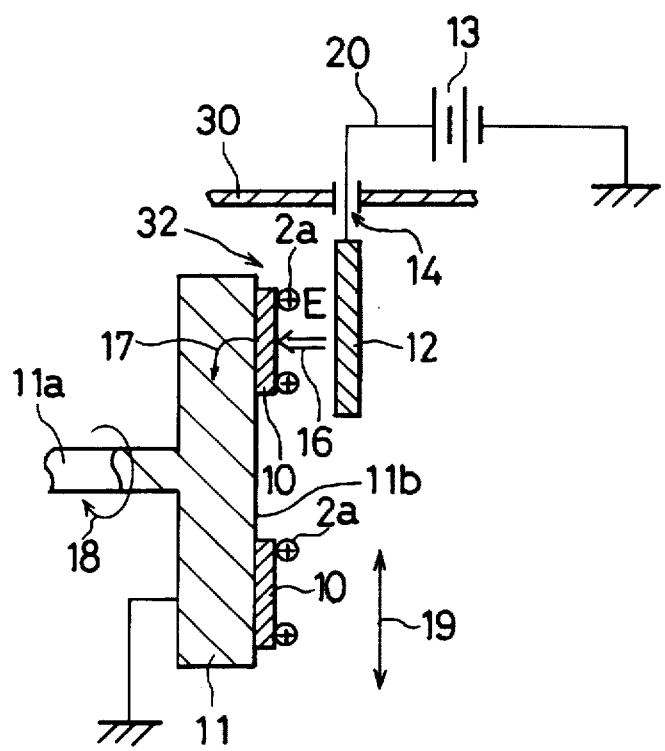
FIG. 4B is a schematic, cross-sectional view of the wafer holder of the ion-implantation system according to the embodiment of FIG. 2, in which the ion-implanted wafer is in the vicinity of the electrode for suppressing the positive charge buildup on the wafer.

As shown in FIG. 2, the rotating wafer disk 11 has an ion-implantation position 31 and a charge-buildup suppressing position 32. The ion-implantation position 31 is located at the top position of the disk 11. The charge-buildup suppressing position 32 is located at a position which is turned around the shaft 11a in a direction of the arrow 18 by an angle θ with respect to the position 31.

Next, an ion implantation method according to an embodiment will be explained below, which is performed with the use of the above-described ion implantation system according to the embodiment.

First, to keep the wafer holder 11 at the ground potential, the holder 11 is connected to the ground. On the other hand, to keep electrode 12 at the potential +V (volt) than the ground, the terminal 12 is electrically connected to the dc power supply 13 through the wiring lines 20.

Next, while rotating the holder 11 around the shaft 11a at the specific speed, the holder 11 is moved vertically upward and downward. At the same time, the beam 15 of the dopant ions 2 is generated and irradiated by the ion-beam irradiation subsystem 9 to one of the wafers 10 held on the disk 11 at the ion-implantation position 31. Thus, the dopant ions 2 are implanted into the wafer 10 with a specific dose.

The ion-implanted one of the wafers 10 is then turned by the angle θ in the direction of the arrow 18 to the charge-buildup suppressing position 32. In this position 32, the ion-implanted one of the wafers 10 is in the vicinity of the flat-plate electrode 12. An electric field 16 is generated between the wafer 10 and the electrode 12 due to the difference between the electric potentials of the wafer 10 and the electrode 12.

If the strength of the electric field 16 is defined as E, it is expressed as $E = V/G$. The field 16 is directed from the electrode 12 to the wafer 10.

The positive charges 2a that have been built up on the surface of the ion-implanted wafer 10 due to the ion-implantation are forced to move toward the bottom of the disk 11 by the electric field 16. The positive charges 2a move as an electric current 17 within the disk 11 to the ground. Thus, the positive charges 2a on the ion-implanted wafer 10 are expelled therefrom because of the electric field 16.

This means that the number of the built-up positive ions 2a on the ion-implanted wafer 10 decreases, thereby suppressing the built-up positive charges 2a from the wafer 10. Therefore, no maintenance of the ion implantation system is necessary, and no inactive time of the ion implantation system occurs, thereby preventing the throughput or productivity of the ion implantation process from decreasing.

Further, since the electric field 16 generated between the electrode 12 and the wafer 10 suppresses the built-up positive charges 2a on the wafer 10, the ion implantation process is able to be performed without the use of the conventional electron shower technique. As a result, the disadvantages that an insulator layer formed on the surface of the wafer 10 is damaged or broken and that the path of the subsequent beam 15 of the dopant ions 2 is deflected cab be deleted.

Since the disk 11 is rotating around the shaft 11a, each of the wafers 10 held on the disk 11 is successively located at the ion-implanted position 31 and the charge-buildup suppressing position 32. Therefore, each of the wafers 10 on the disk 11 is subjected to ion-implantation and then, charge-buildup suppression a plurality of times.

For example, when the ion type is boron ($^{11}B^+$), the acceleration energy of the dopant ions 2 is 40 keV, the dose of the implanted ions 2 is $1\times10^{16}$ cm$^{-2}$, and the beam current of the ions 2 is 7 mA, the number of rotation is designed as 800 rpm, and the dc voltage V is designed as +500 to +1000 volt with respect to the ground.

While the preferred form of the present invention has been described, it is to be understood that modifications will be apparent to those skilled in the art without departing from the spirit of the invention. The scope of the invention, therefore, is to be determined solely by the following claims.

What is claimed is:

1. An ion implantation method comprising the steps of:
   (a) preparing a wafer holder kept at a first electric potential;
   (b) preparing an electrode kept at a second electric potential higher than said first electric potential;
   (c) placing a semiconductor wafer on said holder to be kept at said first electric potential;
   (d) moving said holder so that said wafer held on said holder is located at a first position;
   (e) irradiating a beam of dopant ions to said wafer at said first position to thereby implant said dopant ions into said wafer; and
   (f) moving said holder so that said wafer thus ion-implanted is located at a second position where said wafer is in the vicinity of said electrode;
      an electric field being generated between said wafer and said electrode due to the difference between said first and second electric potentials;
      wherein positive charges that have been built up on a surface of said ion-implanted wafer are expelled therefrom due to said electric field.

2. A method as claimed in claim 1, wherein said wafer holder is formed by a rotatable and movable disk having a shaft and a surface;
   and wherein said disk is rotated around said shaft of said disk and moved along the surface of said disk during an ion-implantation process, so that said beam of said dopant ions scans the whole surface of said wafer.

3. A method as claimed in claim 2, wherein said disk holds another wafer on the surface of said disk so that said two wafers are arranged along a circle concentric with said shaft of said disk at regular intervals.

4. A method as claimed in claim 1, wherein said electrode has a shape like a flat plate whose width is approximately equal to the diameter of said wafer or greater and whose length is approximately equal to the sum of the diameter of said wafer and a stroke length of said movement of said wafer holder.

5. An ion implantation system comprising:
   (a) a vacuum chamber;
   (b) a wafer holder provided in said chamber;
   (c) an ion-beam irradiation subsystem mounted in said chamber;
   (d) an electrode fixed in said chamber;
   (e) said holder being kept at a first electric potential;
   (f) a semiconductor wafer to be ion-implanted being held on said holder to be kept at said first electric potential;
   (g) said holder being movable so that said wafer held on said holder is located at one of a first position and a second position;
   (h) said ion-beam irradiation subsystem generating a beam of dopant ions and irradiating said beam thus generated to said wafer held on said holder at said first position;
   (i) said electrode being kept at a second electric potential higher than said first electric potential;
   (j) said wafer held on said holder being in the vicinity of said electrode at said second position;
      an electric field being generated between said wafer and said electrode due to the difference between said first and second electric potentials; and
   (k) positive charges that have been built up on a surface of said ion-implanted wafer are expelled therefrom due to said electric field.

6. A system as claimed in claim 5, wherein said wafer holder is formed by a rotatable and movable disk having a shaft and a surface;
   and wherein said disk is rotated around the shaft of said disk and is moved along the surface of said disk during an ion-implantation process so that said beam of said dopant ions scans the whole surface of said wafer.

7. A system as claimed in claim 6, wherein said disk holds another wafer on the surface of said disk so that said two wafers are arranged along a circle concentric with said shaft of said disk at regular intervals.

8. A system as claimed in claim 5, wherein said electrode has a shape like a flat plate whose width is approximately equal to the diameter of said wafer or greater and whose length is approximately equal to the sum of said diameter of said wafer and a stroke length of said movement of said wafer holder.

* * * * *